(12) United States Patent
Mathivanan

(10) Patent No.: US 10,150,716 B2
(45) Date of Patent: Dec. 11, 2018

(54) ENDOTHERMIC GAS PHASE CATALYTIC DEHYDROGENATION PROCESS

(71) Applicant: Borealis AG, Vienna (AT)

(72) Inventor: Guhan Mathivanan, Linz (AT)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 15/513,317

(22) PCT Filed: Sep. 22, 2015

(86) PCT No.: PCT/EP2015/071714
§ 371 (c)(1),
(2) Date: Mar. 22, 2017

(87) PCT Pub. No.: WO2016/046199
PCT Pub. Date: Mar. 31, 2016

(65) Prior Publication Data
US 2017/0320795 A1   Nov. 9, 2017

(30) Foreign Application Priority Data
Sep. 23, 2014   (EP) ..................................... 14185959

(51) Int. Cl.
*C07C 5/32* (2006.01)
*C07C 5/327* (2006.01)
(Continued)

(52) U.S. Cl.
CPC ................. *C07C 5/52* (2013.01); *C07C 5/32* (2013.01); *C07C 5/321* (2013.01); *C07C 5/327* (2013.01); *C07C 2523/26* (2013.01)

(58) Field of Classification Search
CPC .. C07C 5/32; C07C 5/333; C07C 5/52; C07C 5/321
See application file for complete search history.

(56) References Cited

U.S. PATENT DOCUMENTS

| 2,419,997 A | 5/1947 | Houdry |
| 5,527,979 A * | 6/1996 | Agaskar ................ C07C 5/3337 585/654 |

(Continued)

FOREIGN PATENT DOCUMENTS

WO   02094750 A1   11/2002

*Primary Examiner* — Youngsul Jeong
(74) *Attorney, Agent, or Firm* — The Webb Law Firm

(57) ABSTRACT

An endothermic catalytic dehydrogenation process conducted in gas phase in system including a reactor with a catalyst bed including an inorganic catalytic material and a first inert material including the steps of: feeding a first stream having an alkane of the formulae I $C_nH_{2n+1}R^1$ with $n \geq 3$ and $R^1 =$ H or aryl to be dehydrogenated into the reactor, and simultaneously or subsequently feeding a second stream including a mixture of an inert gas and a reactive gas selected from the group of alkanes of the formulae II $C_mH_{2m+2}$ with $m \geq 2$, or alkenes of the formulae III $C_mH_{2m}$ with $m \geq 2$. The alkane to be dehydrogenated of formulae I in first stream has at least one more carbon atom than the alkane of formulae II and alkene of formulae III in the second stream.

23 Claims, 1 Drawing Sheet

(51) Int. Cl.
*C07C 5/50* (2006.01)
*C07C 5/52* (2006.01)

(56) References Cited

U.S. PATENT DOCUMENTS

| | | |
|---|---|---|
| 6,756,340 B2 * | 6/2004 | Voskoboynikov ....... B01J 21/04 |
| | | 502/328 |
| 8,653,317 B2 * | 2/2014 | Pierce ...................... B01J 23/62 |
| | | 585/435 |
| 2004/0158110 A1 | 8/2004 | Schweizer et al. |
| 2004/0181104 A1 | 9/2004 | Yeh et al. |
| 2004/0181107 A1 | 9/2004 | Abdulwahed et al. |
| 2007/0054801 A1 | 3/2007 | Fridman et al. |
| 2008/0097134 A1 | 4/2008 | Fridman et al. |
| 2013/0158327 A1 * | 6/2013 | Leonard .................. C07C 5/333 |
| | | 585/655 |

* cited by examiner

ENDOTHERMIC GAS PHASE CATALYTIC DEHYDROGENATION PROCESS

CROSS-REFERENCE TO RELATED APPLICATIONS

This application is the United States national phase of International Application No. PCT/EP2015/071714 filed Sep. 22, 2015, and claims priority to European Patent Application No. 14185959.5 filed Sep. 23, 2014, the disclosures of which are hereby incorporated in their entirety by reference.

BACKGROUND OF THE INVENTION

Field of the Invention

The present invention relates to an endothermic catalytic dehydrogenation process.

Description of Related Art

The invention is concerned with an endothermic hydrocarbon process, particularly for catalytic dehydrogenation of paraffinic and other hydrocarbons such as propane dehydrogenation (reaction 1) or butane dehydrogenation (reaction 2) or i-butane dehydrogenation (reaction 3):

$$C_3H_8 \Leftrightarrow C_3H_6 + H_2 \quad (1)$$

$$C_4H_{10} \Leftrightarrow C_4H_6 + 2H_2 \quad (2)$$

$$i\text{-}C_4H_{10} \Leftrightarrow i\text{-}C_4H_8 + H_2 \quad (3)$$

Dehydrogenation of hydrocarbons, in particular aliphatic hydrocarbons, to convert them into to their respective olefins is a well-known process. For example, the hydrocarbons propane, butane, isobutane, butenes and ethyl benzene are well known catalytically dehydrogenated to produce the respective propylene, butene, isobutene, butadiene and styrene. Dehydrogenation reactions are strongly endothermic and thus, an increase of the heat supply favours the olefin conversion.

One well known dehydrogenation process is the Houdry CATOFIN® process in which an aliphatic hydrocarbon is passed through a dehydrogenation catalyst bed where the hydrocarbon is dehydrogenated to the respective olefin, the olefin is flushed from the bed, the catalyst is regenerated and reduced, and the cycle is repeated (U.S. Pat. No. 2,419,997).

Some other well-known dehydrogenation technologies are Oleflex, Uhde-STAR and BASF-Linde process. Oleflex and CATOFIN technologies are adiabatic processes where the catalyst bed is heated directly. Uhde-STAR and BASF-Linde technologies are isothermal processes where the catalyst bed is heated indirectly.

CATOFIN propane dehydrogenation process is a cyclic process where during regeneration and reduction steps, heat is supplied to the catalyst bed and during dehydrogenation step catalyst bed cools down due to the endothermic dehydrogenation reaction. The upper section of the catalyst gets most of the heat during regeneration and reduction steps and supplies most of the heat to the reaction during the dehydrogenation reaction. On the other hand the heat consumed and supplied by the lower sections of the bed is quite low compared to the upper sections. Propylene production is normally controlled by equilibrium at the bottom section.

Another well-known process is CATADIENE® process in which butanes and butenes are dehydrogenated to produce butadiene.

Propane dehydrogenation reaction is an equilibrium limited reaction. One approach to shift the equilibrium towards the olefin product, such as propylene, can be decreasing the partial pressure of the alkane educt, such as propane. This can be achieved by adding a suitable diluent gas.

For example US 2004/0181107 A1 discloses the addition of carbon dioxide providing an in situ heat source for the reaction, decreases coke formation, enhances olefin selectivity and extends the dehydrogenation catalytic cycle. In addition an inert diluent, such as methane, or nitrogen may be added.

WO 2002/094750A1 proposes adding a diluent along with a source of halogen for the process of oxidative halogenations. US2004/0181104 A1 discloses the addition of an olefin to the dehydrogenation process to consume hydrogen and to shift equilibrium of dehydrogenation reaction.

US 2013/158327A1 suggests the addition of pure methane as inert diluent to the alkane feed for improving the yield of olefin in dehydrogenation process. The feed stream also contains hydrogen along with the alkane and inert diluent. The inert diluent increases the propylene yield of propane dehydrogenation process. However, a drawback of this approach is the availability and high cost of pure methane.

Thus, it would be of an advantageous to provide a process for improving conversion of a gas phase dehydrogenation process without having the above described drawbacks. It would be in particular of an advantageous to use a system which can improve the propylene yield of propane dehydrogenation reaction and is at the same time cost-efficient.

SUMMARY OF THE INVENTION

Accordingly, an endothermic catalytic dehydrogenation process conducted in gas phase in at least one reactor system comprising at least one reactor with at least one catalyst bed comprising at least one inorganic catalytic material and at least one first inert material.

The dehydrogenation process comprises the steps of:
  feeding at least one first stream comprising at least one alkane of the general formulae I $C_nH_{2n+1}R^1$ with $n \geq 3$ and $R^1 = H$ or aryl to be dehydrogenated into the at least one reactor, and
  simultaneously or subsequently feeding at least one second stream comprising a mixture of at least one inert gas and at least one reactive gas selected from the group of alkanes of the general formulae II $C_mH_{2m+2}$ with $m \geq 2$, or alkenes of the general formulae III $C_mH_{2m}$ with $_m \geq 2$,
  wherein the alkane to be dehydrogenated of the general formulae I in the at least one first stream S1 comprises at least one more carbon atom than the alkane of the general formulae II and alkene of the general formulae III in the at least one second stream S2

Thus, it is to be understood that the alkane (to be dehydrogenated) of the first stream differs from the alkane of the second stream. In particular, the alkane to be dehydrogenated in the first stream comprises at least one more carbon atom than the alkane in the second stream.

According to the invention a gas mixture of at least one inert gas and an alkane and/or alkene (olefin) is fed as a diluent gas whereby reducing the partial pressure of the alkane to be dehydrogenated in the first stream. This in turn provides a positive impact since the reaction favors a lower partial pressure of the alkane to be dehydrogenated. Furthermore, it can add additional heat to the process due to the increased heat capacity. The alkane of formulae II such as ethane may be dehydrogenated and the alkene of formulae III such as ethen may be hydrogenated during the overall dehydrogenation process. The alkane dehydrogenation/alkene hydrogenation depends on the molar ratio of alkane:alkene in the second stream and the temperature of the system. Thus, alkane and alkene of the second stream S2 may also be seen as reactive gases; for example in case of ethane and ethen as C2 reactive gas.

In an embodiment of the present process in the general formulae I of the alkane to be dehydrogenated is n=3-20, preferably 3-10, most preferably 3-8; and $R^1$=H or $C_6$-$C_{20}$ aryl, preferably $C_6$-$C_{10}$ aryl, most preferably $C_6$ or $C_{10}$ aryl. The alkane of general formulae I to be dehydrogenated can thereby be linear or branched. It is preferred if the alkane of general formulae I is selected from a group comprising propane, butane, iso-butane, tert-butane, pentane, iso-pentane, hexane, ethyl benzene and mixtures thereof. The mostly preferred alkanes to be dehydrogenated are propane, iso-butane and ethyl benzene.

In a preferred embodiment of the present process the at least one inert gas in the second mixture stream are selected from a group comprising methane, nitrogen, argon or helium.

An inert gas within the meaning of the present invention is a gas which does not adversely affect the dehydrogenation process. In particular preferred inert gas is methane.

In a further embodiment of the present process in the alkane of general formulae II or alkene of general formulae III (or mixtures thereof) in the gas mixture to be co-fed (second stream) is: m=2-19, preferably 2-9, most preferably 2-7. It is also possible that the alkane and/or alkene (olefin) can be linear or branched such as for example tert-butylethene.

It is preferred if the alkane of general formulae II is selected from a group comprising ethane, propane, butane, pentane, hexane and mixtures thereof. It is however understood as mentioned previously that the alkane to be dehydrogenated of general formulae I in the first stream and the alkane of general formulae II in the second stream differ from each other. The mostly preferred alkane to be co-fed is ethane.

It is preferred if the alkene (olefin) of general formulae III is selected from a group comprising ethene, propene, butene, pentene, hexene and mixtures thereof. The mostly preferred olefin to be co-fed is ethene.

As mentioned previously, the alkane (to be dehydrogenated) of the general formulae I in the at least one first stream comprises at least one more carbon atom than the alkane of the general formulae II and alkene (olefin) of the general formulae III in the at least one second stream, i.e. the alkane of formulae I in the first stream has a higher molar mass or molecular weight than the alkane of formulae II or alkene of formulae III in mixture of the second stream.

Thus, in the present process the alkane or hydrocarbon to be dehydrogenated can be co-fed with an alkene and/or alkane, which has at least one carbon atom less than the alkane to be dehydrogenated. For example, propane (C3) to be dehydrogenated to propene is co-fed with ethane (C2) and/or ethene (C2). Even when using a mixture of alkanes and alkenes in the second stream only such components are selected which have less carbon atoms than the alkane(s) to be dehydrogenated.

In a further embodiment of the present process the molar ratio of the at least one inert gas and the at least one alkane/alkene in the second mixture stream is between 99.9:0.1 and 0.1:99.9, preferably between 99:1 and 1:99; more preferably between 90:10 and 10:90, most preferably between 80:20 and 20:80, in particular preferably between 70:30 and 30:70. The ratio can thus also be 50:50. However, it is mostly preferred to use a gas mixture comprising an excess of inert gases, such as a mixture having a molar ratio of 70:30 or 80:20 of inert gases to alkane/alkene.

In yet another embodiment of the present process in case an inert gas and a mixture of alkane and alkene is used as second stream alkane and alkene have a varying molar ratio to each other. For example it is conceivable to use the alkane in excess to the alkene or vice versa.

In a most preferred embodiment of the present process a mixture comprising methane, ethane and ethene is used as second stream. In particular a mixture of 20 mol % methane, 50 mol % ethane and 30 mol % ethene is used. One advantage of this specific gas mixture is that the products present in this mixture are byproducts of propane dehydrogenation process. Furthermore, as will be shown in the Examples further below such a gas mixture as diluent can be surprisingly more beneficial than using a pure inert (pure methane) as a diluent.

In yet a further embodiment of the present process the second stream S2 may comprise (besides inert gas, alkane, alkene) also further additional compounds or impurities such as propane. This is mainly due to the source of the reactive gas such as a byproduct of the propane dehydrogenation process. The amount of such further additional compounds in stream S2 may be up to 20%, preferably less than 10%.

In another variant the present process is characterized by a total dehydrogenation time $tS_{1(E)}$, wherein the at least one first stream comprising the at least one alkane of the general formulae I is fed into the at least one reactor for a total alkane feeding time $tS_1$ and the at least one second stream S2 comprising the mixture of at least one inert gases and the at least one alkane of the general formulae II and/or the at least one alkene of the general formulae III is fed into the at least one reactor for a total feeding time $tS_2$, wherein the ratio z of total feeding time $tS_2$ and total feeding time $tS_1$ is between 0.001 and 1, preferably 0.005 and 0.95, more preferably between 0.01 and 0.5, most preferably between 0.05 and 0.1. It is to be understood that the ratio z of total feeding time $tS_2$ and total feeding time $tS_1$ is influenced by the amount or percentage of alkene such as ethene in the second stream mixture S2; i.e. the higher the amount of alkene the more the time point of feeding the second stream S2 to the first stream S1 shifts to the end of the total feeding time. This is due to the coke formation caused by the higher percentage of alkene such as ethene in the second stream S2. If the amount or percentage of alkene in the second stream S2 is lower than the diluent or second stream may be fed at an earlier time point.

Within the context of the present invention it will be understood that the ratio of total mixture feeding time $tS_2$ and total feeding time $tS_1$ is imperatively below 1. This means that the total mixture feeding time $tS_2$ is always smaller or shorter than the total alkane feeding time $tS_1$. Thus, the beginning of mixture feeding is imperatively delayed in respect to alkane feeding time. The gas mixture is not immediately fed together with the alkane stream to the dehydrogenation reactor, but rather with a time delay. The second mixture stream is only fed to the reactor after dehydrogenation reaction of the alkane in the catalyst bed has already started.

This can also be described such that the alkane feeding is started at a time point $tS_{1(O)}$, and ends at a time point $tS_{1(E)}$ providing $tS_1=tS_{1(E)}-tS_{1(O)}$; and the mixture feeding is started at a time point $tS_{2(O)}$ and ends at a time point $tS_{2(E)}$ providing $tS_2=tS_{2(E)}-tS_{2(O)}$.

The time point $tS_{2(O)}$ for the start of feeding the mixture stream S2 is provided after time point $tS_{1(O)}$, for the start of feeding the alkane stream S1 such that $tS_{2(O)}=tS_{1(O)}+x$, wherein x is any possible time interval above 0 sec. The time difference between feeding the alkane stream and the mixture stream can be of any x value, such for instance at least 30 sec, at least 1 min or at least 5 min (provided that the above ratio of $tS_2:tS_1$ is full filled). For example, if x is 1 min and $tS_1$ is 10 min and $tS_2$ is 9 min then the ratio of $tS_2:tS_1$ would be 0.9.

In an embodiment total continuous alkane feeding S1 (or dehydrogenation) begins at $tS_{1(0)}$ and ends at $tS_{1(E)}$. mixture feeding S2 is started at $tS_{2(0)}$ after a certain dehydrogenation time $tS_{1(1)}$, i.e. $tS_{1(1)} = tS_{2(0)} = tS_{1(0)} + x = S_{1(E)} - tS_{2(E)}$. The mixture feeding S2 may then be continued until the dehydrogenation reaction is ended, e.g. for instance until $tS_{1(E)}$ is reached. In this case alkane and mixture are fed together starting at $tS_{2(0)}$.

It is also possible to interrupt the mixture feeding S2 at any time value y, for instance at $tS_{2(1)} = tS_{2(0)} + y$ for a time (or break) value z and to restart the mixture feeding at $tS_{2(2)} = tS_{2(0)} + (y+z)$. Such an interruption of mixture feeding would have the advantage of reducing the overall coke formation.

It is furthermore possible to stop the mixture feeding before the end of dehydrogenation at $tS_{1(E)}$. For instance in the last minute of the dehydrogenation reaction there is no mixture feed necessary, since the additional heat created by the olefin (as part of the mixture) hydrogenation would be lost.

In another preferred variant of the present process the first stream S1 is fed to the at least one reactor of the reactor system as front feed and the second mixture stream S2 is fed to the at least one reactor of the reactor system at at least one location alongside of the at least one reactor.

In a preferred embodiment the two process variants can be also combined, i.e. the time and local adaption of alkane and mixture feeding can be combined.

Thus, in a single reactor system, mixture feeding can be done at the top of catalyst bed or at the deeper bed and either can be fed from the beginning of dehydrogenation step or after few minutes of the dehydrogenation step. The timing and the place to feed the mixture can be freely chosen.

In an embodiment of the processes the second mixture stream S2 is fed along the at least one reactor of the reactor system at at least one of the following locations: top of the catalyst bed, first half of the catalyst bed and second half of the catalyst bed.

A yet another effect of feeding a mixture stream (for example together with or delayed to the alkane feed or at any location alongside of the reactor) is an extension of the total dehydrogenation time $tS_1$. This is due to the fact that the olefin feeding reduces the temperature drop over the catalyst bed as described above.

In a further variant of the present process a layer of a second inert material, which may be the same as the first inert material or different from the first inert material, is arranged upstream and/or downstream of the catalyst bed.

One preferred arrangement is that the layer of a second inert material is disposed on top or on the upper surface of the catalyst bed which is usually arranged in a horizontal manner. The layer of second inert material and the catalytic material are in direct contact with each other. The layer of the second inert material may have approximately a thickness D in a range between 10 cm and 100 cm, preferably 15 cm and 60 cm, most preferably between 20 and 40 cm.

Another possible arrangement is that the second inert material is arranged in an extra vessel which is being upstream of the dehydrogenation reactor. Thus, the layer of second inert material and the catalytic material are not in direct contact with each other; they are rather spatially separated. Thus, in another embodiment of the present catalyst bed system the predetermined volume of the second inert material is arranged in at least one extra vessel, which is arranged upstream of the reactor. In this case the volume of the second inert material in the at least one vessel may be between 15 and 180 tons, preferably 20 and 110 tons and most preferably 30 and 70 tons.

In an embodiment of the processes the second mixture stream S2 is fed to the at least one layer of a second inert material arranged upstream and/or downstream of the at least one catalyst bed in the at least one reactor.

In a variant of the process the temperature of the alkane feed and of the mixture feed are between 400 and 650° C., preferably 500 and 650° C., most preferably 550 and 650° C., respectively.

The reaction temperatures in the catalyst bed may be between 500 and 1000° C., preferably between 500 and 800° C., most preferably between 500 and 700° C. The catalyst bed is heated by introducing a heat stream for heating and/or regenerating the catalytic material.

The heat stream preferably comprises a hot air stream or air feed and an injection gas feed. Thus, the temperature of the heat stream is preferably the temperature resulting from the combustion of air and injection gas. It is however in general conceivable to increase the heat input also by other measures. For instance, heat can be provided in a direct manner such as by combustion of fuel gas or in an indirect manner by heating air without combustion gas. It is furthermore conceivable to increase the heat input into the catalytic bed also by measures such as heating the reactor mantle. That means heating measures from the inside or the outside of the reactor are possible. It is also conceivable to add the heat within the reactor or before air enters the reactor.

The hot air stream may be fed at a rate between 100 and 500 Mt/hr, preferably between 150 and 400 Mt/hr, most preferably between 200 and 300 Mt/hr, whereby 210 Mt/hr is the typical applied feed rate.

The injection gas stream can be fed with a rate between 0.1 and 0.6 kg/sec preferably between 0.1 and 0.4 kg/sec, most preferably between 0.1 and 0.2 kg/sec, whereby 0.125 kg/sec is the typical fed rate. Thereby the fed rate of the injection gas stream depends strongly on the operational mode as described above.

In general the present process may be conducted at a pressure in a range between 100 mmHg to 750 mmHg.

The first alkane stream S1 may be fed at a rate between 20 and 60 Mt/hr, preferably between 25 and 50 Mt/hr, most preferably between 35 and 50 Mt/hr.

The flow rate of the mixture feed S2 is between 500 kg/h and 30 t/h, preferably between 1 and 20 t/h, most preferably between 2 and 10 t/h.

The molar ratio of the first alkane stream S1 and the second stream S2 is between 50 and 1, preferably between 45 and 3, most preferably between 30 and 15. Thus, the first alkane stream S2 is preferably fed in excess to the olefin.

The inorganic catalytic material of the catalyst bed is preferably selected from a group consisting of chromium oxide, platinum, iron, vanadium and their respective oxides or a mixture thereof.

The first inert material of the catalyst bed is preferably selected from the group consisting of magnesium oxide, aluminium oxide, aluminium nitride, titanium oxide, zirconium dioxide, niobium oxide, aluminium silicate and others. The inert material may not only serve as heat storing material but also may have the function of a support system.

In the context of the present invention "inert material" is defined as a material which does not exhibit any catalytic effect in the dehydrogenation reaction, but may participate in other reactions such as cracking or coking which take place during dehydrogenation.

The catalyst bed comprises preferably 50 Vol % of a catalytic material and 50 Vol % of a first inert material. However, in case of isobutane dehydrogenation 70 Vol % catalytic materials is mixed with 30 Vol % inert materials (see US 2007/054801 A1).

A typical Chromium oxide dehydrogenation catalyst manufactured on an alumina support comprises from about 17 wt % to about 22 wt % $Cr_2O_3$. These type of dehydrogenation catalyst are known for instance under the name Catofin® Standard catalyst (US 2008/0097134 A1). It is to be understood that the concept of the present process—namely the use of an extra inert layer—is applicable to any type of dehydrogenation catalyst and not only to the ones explicitly mentioned within the context of this application. Thus, all other commonly used dehydrogenation catalysts may also be applicable.

The catalyst bed is prepared by mixing or combining the catalytic material and the first inert material. The required amount of catalytic material is determined and is then mixed with a defined amount of first inert material. The catalyst bed is evacuated and reduced with hydrogen. Then an aliphatic hydrogen carbon such as propane, butane, isobutane or an aromatic alkane such as ethyl benzene is fed to the catalyst bed and is dehydrogenated upon contact with the catalytic material to the corresponding unsaturated alkanes such as propylene, butadiene, isobutene or styrene.

The present dehydrogenation process may be conducted in a single reactor with multiple tubes or in multiple parallel reactors as in CATOFIN process. Also it can be conducted in multiple serial reactors as in Oleflex process.

In a preferred embodiment the present dehydrogenation process is conducted in a reactor system comprising at least two reactors, which are connected in series, and which comprise at least one first catalyst bed comprising at least one inorganic catalytic material and at least one first inert material, respectively.

This preferred arrangement can be seen as the spatial separation of the catalyst bed into its upper section (which receives most of the heat during regeneration and reduction of the catalyst bed and thus supplies most of the heat to the dehydrogenation reaction) located in the first reactor and its lower section (which receives and provides less heat to the dehydrogenation reaction accordingly) located in the second reactor. In case the olefin stream S2 is fed into the first reactor the additional heat provided by the exothermic hydrogenation reaction of the olefin is preferably distributed to both reactors. In this way the temperature drop in both reactors is decreased. The degree of the temperature drop depends on the amount of olefin stream S2 supplied to the first reactor. In case the olefin stream S2 is supplied to the second reactor, the temperature drop in the second reactor alone will be decreased and as the result the temperature in the second reactor will have the same or a higher temperature than the first reactor.

In an embodiment of said multiple reactor arrangement for conducting the present process the at least one first alkane stream S1 is fed solely into the first reactor and is only mixed with the at least one second mixture stream S2 after leaving the first reactor and before entering the second reactor. Thereby it is preferred if the at least one first alkane stream S1 is fed into a first reactor as front feed and the at least one second mixture stream S2 is fed into the gas stream leaving the first reactor at at least one location between the first reactor and the second reactor. It is also possible that the at least one mixture stream S2 is fed to the reactor system at at least one location alongside of the first reactor and/or the second reactor.

It is furthermore preferred if the at least one alkane stream leaving the first reactor (intermediate effluent stream) having a reduced temperature due to the heat consumption during the endothermic dehydrogenation is re-heated by passing at least one heater and the heated intermediate effluent stream leaving the heater is fed into the second reactor.

It is also possible that the at least one second mixture stream is heated before entering the second reactor. Thus, the at least one mixture stream for example methane-ethane-ethene stream may be introduced into the heater and may be thereby be mixed with the intermediate effluent stream in the heater or before entering the heater. In the latter case a mixed stream of intermediate effluent stream and olefin is fed into the heater.

Both, the heating of the alkane and the mixture stream may be carried out in a heater arranged between the first reactor and the second reactor.

The mixed stream of intermediate effluent stream and gas mixture is—after leaving the heater-subsequently fed into the second reactor wherein further dehydrogenation reaction of the non-saturated alkane such propane to the corresponding olefin such as propene takes place. The hydrogen released during the dehydrogenation reaction reacts provides additional heat which is used in turn for the endothermic dehydrogenation reaction.

Furthermore, the present process does not depend on a specific reactor cycle. Thus, the present process can be used in all dehydrogenation cycle lengths, regeneration cycle lengths and/or reduction phase length.

BRIEF DESCRIPTION OF THE DRAWINGS

The present invention is further explained in more detail based on the following examples in conjunction with the Figures. It shows.

DETAILED DESCRIPTION OF THE INVENTION

Figure 1:
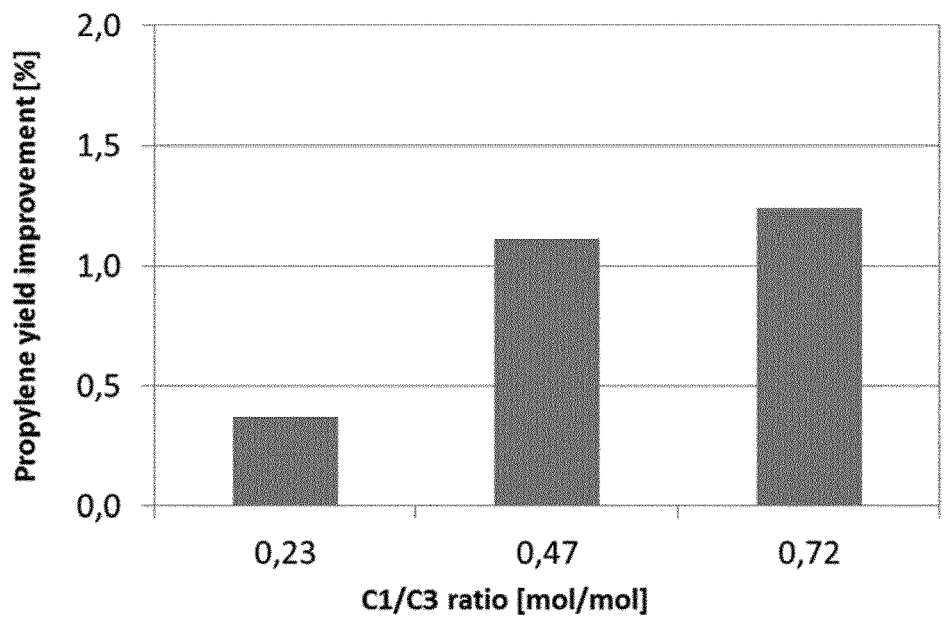
FIG. 1 a first diagram showing the influence of a diluent according to prior art to the dehydrogenation process.
Figure 2:
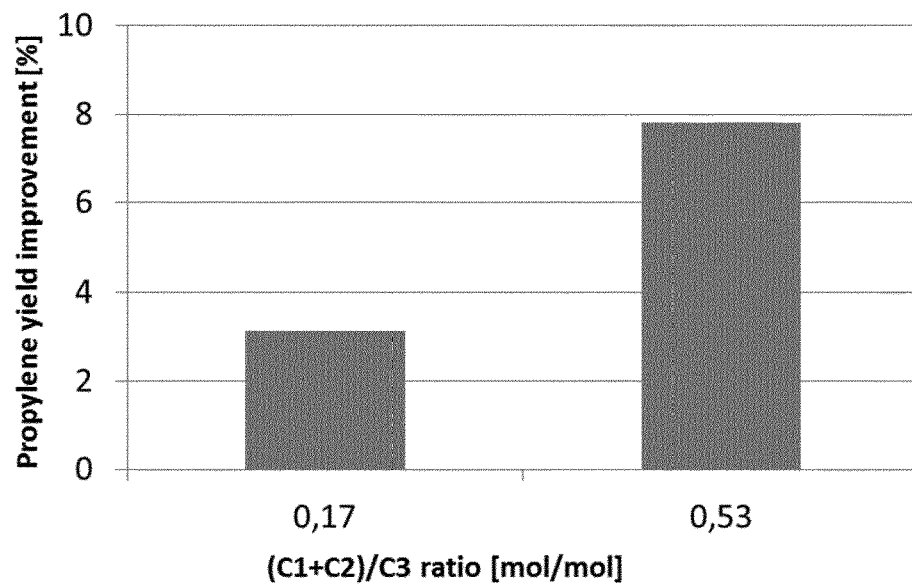
FIG. 2 a second diagram showing the influence of a diluent according to an embodiment of the present invention.

The following examples show the propylene yield improvement that can be made using methane as a diluent or methane-ethane-ethylene as a diluent. From FIGS. 1 and 2 one can see that using methane-ethane-ethylene gas mixtures as a diluent is more beneficial than using methane alone as a diluent in terms of propylene yield improvement. Increasing the methane-ethane-ethylene amount increases the yield improvement.

The composition of methane-ethane-ethylene gas mixture is shown in table 1.

TABLE 1

Composition of methane-ethane-ethylene gas mixture

| Component | Mole % |
|---|---|
| Methane | 20 |
| Ethane | 50 |
| Ethylene | 30 |

TABLE 2

Experimental conditions and yield improvement while using methane as diluent

| | Base case | Methane diluent | | |
|---|---|---|---|---|
| C1/C3 ratio, mol/mol | 0 | 0.23 | 0.47 | 0.72 |
| Total pressure, bar | 1.7 | 1.7 | 1.7 | 1.7 |
| Temperature, ° C. | 600 | 600 | 600 | 600 |
| Yield improvement per pass, mol % | — | 0.4 | 1.1 | 1.2 |

TABLE 3

Experimental conditions and yield improvement while using methane-ethane-ethylene gas mixture as diluent

| | Base case | Methane-Ethane-Ethylene diluent | |
|---|---|---|---|
| (C1 + C2)/C3 ratio, mol/mol | 0 | 0.17 | 0.53 |
| Total pressure, bar | 1.7 | 1.7 | 1.7 |
| Temperature, ° C. | 600 | 600 | 600 |
| Yield improvement per pass, mol % | — | 3.12 | 7.8 |

50 grams of catalyst was loaded in a fixed bed reactor. Reactor was heated externally by an electrical heating oven. The reactor effluents were analysed by a GC and online CO, $CO_2$ and hydrogen sensors. Nitrogen was introduced with the reactant at constant rate. After the dehydrogenation step, reactor was flushed and regenerated by air.

The invention claimed is:

1. An endothermic catalytic dehydrogenation process conducted in gas phase in at least one reactor system comprising at least one reactor with at least one catalyst bed comprising at least one inorganic catalytic material and at least one first inert material comprising the steps of:
   feeding at least one first stream comprising at least one alkane to be dehydrogenated of a general formula I $C_nH_{2n+1}R^1$ with n=3-8 and $R^1$=H or aryl into the at least one reactor, and
   simultaneously or subsequently feeding at least one second stream comprising a diluent gas mixture of (i) at least one inert gas, (ii) at least one reactive gas selected from the group of alkanes of a general formula II $C_mH_{2m+2}$ with m=2-7, and (iii) at least one reactive gas selected from the group of alkenes of a general formula III $C_mH_2$, with m=2-7,
   wherein the at least one alkane to be dehydrogenated of the general formula I in the at least one first stream comprises at least one more carbon atom than the alkane of the general formula II and the alkene of the general formula III in the at least one second stream, such that the alkane of general formula I in the first stream S1 and the alkane in the second stream S2 differ from each other,
   and wherein a molar ratio of the alkane in the at least one first stream S1 to a mixture of the at least one second stream S2 is between 50:1 and 1:1.

2. The process according to claim 1, wherein in the alkane of the general formula I, n=3-8 and $R^1$=H or $C_6$-$C_{20}$ aryl.

3. The process according to claim 1, wherein the alkane of the general formula I comprises propane, butane, iso-butane, pentane, iso-pentane, hexane, ethyl benzene or mixtures thereof.

4. The process according to claim 1, wherein the at least one inert gas comprises methane, nitrogen, helium or argon.

5. The process according to claim 1, wherein in the alkane of the general formula II and/or the alkene of the general formula III, m=2-6.

6. The process according to claim 1, wherein the alkane of the general formula II comprises ethane, propane, butane, pentane, hexane or mixtures thereof and the alkene of the general formula III comprises ethene, propene, butene, pentene, hexene or mixtures thereof.

7. The process according to claim 1, wherein a molar ratio of the at least one inert gas to the at least one reactive gas selected from the group of alkanes of the general formula II and/or the at least one reactive gas selected from the group of alkenes of the general formula III in the at least one second stream is between 99.9:0.1 and 0.1:99.9.

8. The process according to claim 1, wherein the at least one alkane of the general formula II and the at least one alkene of the general formula III used in the mixture of the at least one second stream S2 have different moles.

9. The process according to claim 1, wherein the mixture of the at least one second stream S2 comprises methane, ethane and ethene.

10. The process according to claim 1, comprising a total dehydrogenation time, wherein the at least one first stream is fed into the at least one reactor for a total alkane feeding time $tS_1$ and the at least one second stream is fed into the at least one reactor for a total feeding time $tS_2$, wherein a ratio z of the total feeding time $tS_2$ to the total alkane feeding time $tS_2$ is between 0.001 and 1.

11. The process according to claim 1, wherein the at least one first stream is fed to the at least one reactor of the at least one reactor system as front feed and the at least one second stream is fed to the at least one reactor of the at least one reactor system at least one location alongside of the at least one reactor.

12. The process according to claim 1, wherein at least one layer of a second inert material is arranged upstream and/or downstream of the at least one catalyst bed in the at least one reactor.

13. The process according to claim 1, wherein the at least one reactor system comprises at least two reactors, which are connected in series and comprise at least one catalyst bed comprising at least one inorganic catalytic material and at least one first inert material, respectively.

14. The process according to claim 1, wherein a temperature of a feed of the at least one first stream and of a feed of the at least one second stream are between 400 and 650° C. respectively, and reaction temperature(s) in the at least one catalyst bed is/are between 500 and 1000° C.

15. The process according to claim 1, wherein the at least one inorganic catalytic material of the at least one catalyst bed comprises chromium oxide, platinum, iron, vanadium or a mixture thereof and the at least one first inert material of the at least one catalyst bed comprises magnesium oxide, aluminium oxide, aluminium nitride, titanium oxide, zirconium dioxide, niobium oxide or aluminium silicate.

16. The process according to claim 2, wherein n=3-8 and $R^1$=H or $C_6$-$C_{10}$ aryl.

17. The process according to claim 7, wherein the molar ratio of the at least one inert gas to the at least one reactive gas selected from the group of alkanes of the general formula II and/or the at least one reactive gas selected from the group of alkenes of the general formula III in the at least one second stream is between 70:30 and 30:70.

18. The process according to claim 9, wherein the mixture of the at least one second stream S2 comprises 20 mol % methane, 50 mol % ethane, and 30 mol % ethene.

19. The process according to claim 10, wherein the ratio z of the total feeding time $tS_2$ to the total alkane feeding time $tS_1$ is between 0.05 and 0.1.

20. The process according to claim 1, wherein the molar ratio of the alkane in the at least one first stream S1 to the mixture of the at least one second stream S2 is between 45:1 and 3:1.

21. The process according to claim 1, wherein the molar ratio of the alkane in the at least one first stream S1 to the mixture of the at least one second stream S2 is between 30:1 and 15:1.

22. The process according to claim 7, wherein the molar ratio of the at least one inert gas to the alkane of the general formula II and the alkene of the general formula III in the at least one second stream is between 80:20 and 20:80.

23. The process according to claim 7, wherein the molar ratio of the at least one inert gas to the alkane of the general formula II and the alkene of the general formula III in the at least one second stream is between 70:30 and 30:70.

* * * * *

UNITED STATES PATENT AND TRADEMARK OFFICE
CERTIFICATE OF CORRECTION

PATENT NO. : 10,150,716 B2
APPLICATION NO. : 15/513317
DATED : December 11, 2018
INVENTOR(S) : Guhan Mathivanan Page 1 of 1

It is certified that error appears in the above-identified patent and that said Letters Patent is hereby corrected as shown below:

In the Claims

Column 9, Line 59, Claim 1, delete "$C_mH_2$," and insert -- $C_mH_{2m}$ --

Column 10, Line 40, Claim 10, delete "$tS_2$" and insert -- $tS_1$ --

Signed and Sealed this
Sixteenth Day of April, 2019

Andrei Iancu
*Director of the United States Patent and Trademark Office*